United States Patent
Jando

(10) Patent No.: US 10,935,430 B2
(45) Date of Patent: Mar. 2, 2021

(54) INTEGRATED TEMPERATURE SENSOR ON LEAD SELENIDE PLATE DETECTOR ASSEMBLY

(71) Applicant: KONINKLIJKE PHILIPS N.V., Eindhoven (NL)

(72) Inventor: Szilveszter Cseh Jando, Naugatuck, CT (US)

(73) Assignee: Koninklijke Philips N.V., Eindhoven (NL)

(*) Notice: Subject to any disclaimer, the term of this patent is extended or adjusted under 35 U.S.C. 154(b) by 54 days.

(21) Appl. No.: 16/475,768

(22) PCT Filed: Jan. 3, 2018

(86) PCT No.: PCT/EP2018/050101
§ 371 (c)(1),
(2) Date: Jul. 3, 2019

(87) PCT Pub. No.: WO2018/130436
PCT Pub. Date: Jul. 19, 2018

(65) Prior Publication Data
US 2019/0346309 A1 Nov. 14, 2019

Related U.S. Application Data

(60) Provisional application No. 62/444,847, filed on Jan. 11, 2017, provisional application No. 62/511,485, filed on May 26, 2017.

(51) Int. Cl.
*G01N 21/49* (2006.01)
*G01J 5/06* (2006.01)
(Continued)

(52) U.S. Cl.
CPC .............. *G01J 5/061* (2013.01); *G01J 5/046* (2013.01); *G01N 21/3504* (2013.01);
(Continued)

(58) Field of Classification Search
CPC .......... G01J 1/42; G01J 1/44; G01J 2005/063; G01J 2005/068; G01J 3/42; G01J 5/046;
(Continued)

(56) References Cited

U.S. PATENT DOCUMENTS 4,142,198 A * 2/1979 Finnila .............. H01L 27/14875
257/227
5,464,982 A 11/1995 Drucker et al.
(Continued)

FOREIGN PATENT DOCUMENTS

DE 102011056610 A1 6/2013
WO 2015159176 A1 10/2015

OTHER PUBLICATIONS

International Search Report and Written Opinion, International Application No. PCT/EP2018/050101, dated May 24, 2018.

*Primary Examiner* — Irakli Kiknadze
(74) *Attorney, Agent, or Firm* — Michael W. Haas

(57) ABSTRACT

An improved infrared-based gas detector apparatus is described in which a substantial improvement in temperature measurement and tracking accuracy is achieved by combining a temperature sensing element such as a Thermistor to the body of a Lead Selenide (PbSe) plate detector. This allows for as close to possible measurement of the actual Lead Selenide film temperature without coming directly in physical contact with the film surface itself.

18 Claims, 5 Drawing Sheets

(51) Int. Cl.
*G01J 5/04* (2006.01)
*G01N 21/3504* (2014.01)
*G01N 33/00* (2006.01)

(52) U.S. Cl.
CPC ...... *G01N 33/004* (2013.01); *G01J 2005/063* (2013.01); *G01J 2005/068* (2013.01)

(58) Field of Classification Search
CPC ... G01J 5/061; G01N 21/3504; G01N 33/004; H01L 2924/00; H01L 2924/0002; H01L 2224/48091; H01L 2924/00014; H01L 2924/01015; H01L 2924/01047; H01L 2924/1305; H01L 2924/13091; H01L 2924/1461; H01L 2924/181; H01L 2924/30107; H01L 2924/3011; H01L 2924/3025; H01L 51/4253; H01L 51/0005; H01L 51/424; H01L 2924/00012; H01L 2224/48247; H01L 23/53285; H01L 2924/10253; G01K 7/006; G01L 21/12; H01F 6/06; H02K 3/02; H02K 55/00; H05K 3/102; H05K 3/125; C04B 35/45; H01B 1/00; H01R 13/6683; H01R 33/945; H05B 45/20
USPC .................................................... 250/338.5
See application file for complete search history.

(56) References Cited

U.S. PATENT DOCUMENTS

| | | |
|---|---|---|
| 6,626,835 B1 | 9/2003 | Kraus |
| 2004/0065829 A1 | 4/2004 | Burk et al. |
| 2007/0296955 A1* | 12/2007 | Skultety-Betz .......... G01V 8/00 356/51 |
| 2008/0224046 A1 | 9/2008 | Ogando et al. |
| 2009/0140149 A1 | 6/2009 | Tinnes |
| 2012/0286161 A1* | 11/2012 | Raieszadeh ............... G01J 5/58 250/338.3 |
| 2013/0292570 A1 | 11/2013 | Gerety et al. |

* cited by examiner

INTEGRATED TEMPERATURE SENSOR ON LEAD SELENIDE PLATE DETECTOR ASSEMBLY

Cross-Reference to Prior Applications

This application is the U.S. National Phase application under 35 U.S.C. § 371 of International Application No. PCT/EP2018/050101, filed on 3 Jan. 2018, which claims the benefit of U.S. Provisional patent application Ser. No. 62/444847, filed on 11 Jan. 2017 and 62/511485, filed on 26 May 2017. These applications are hereby incorporated by reference herein.

The invention relates to an improved gas detection apparatus and method for a substantial improvement in temperature measurement and tracking accuracy, which is achieved by combining a temperature sensing element such as a Thermistor close to the body of an infrared (IR)-sensitive detector such as a Lead Selenide (PbSe) film plate detector. The object of the improvement is to allow for as close as possible measurement of the actual film temperature without coming directly in physical contact with the film surface itself. An embodiment of the apparatus is a carbon dioxide gas detector in a capnography system.

Many capnography systems use two IR detectors, such as Lead Selenide detectors. One detector is for detecting a sample gas absorption wavelength and the other detector senses a reference wavelength. Both detectors must be closely monitored for any small changes in temperature between the two detectors. One example of such a capnography system is described in co-assigned U.S. Patent Publication No. 2013/0292570 entitled "System and method for performing heater-less lead selenide-based capnometry and/or capnography", which is herein incorporated by reference.

Prior art capnography systems such as the example provided also sense temperature at the detector by placing a thermistor in proximity to the lead selenide plate detector, typically mounted onto a substrate surface in which the detector body is mounted onto. Unfortunately, this arrangement introduces a large thermal gradient and an associated large thermal lag time between the thermistor sensor and the film temperature of the lead selenide plate detector because the substrate on which the film is deposited is made of fused quartz, a poor thermal conductor.

Thus what is needed is a more accurate and faster response detection of the lead selenide plate detector, especially as to the effects of temperature variation, which avoids the problems presented by the prior art.

The invention described here has utility in particular for carbon dioxide gas detection and measurement as well as for detection and measurement of any other gas with absorption wavelengths in the mid-wave infrared spectral band. The inventors have discovered an ingenious and novel arrangement of a temperature sensor with respect to an IR-sensitive detector film. Such a temperature sensor can be a microminiature chip thermistor. In addition, with the chip thermistor mounted to each of the two detectors any small differential temperatures between the two detectors can then be detected and algorithmically compensated for to maintain the capnography system CO2 accuracy. This technique can also be used on any other detector material or assemblies in which two electrical terminals exist in close proximity to the detector sensing material.

The inventive approach to increasing the temperature measurement and temperature tracking accuracy of a detector such as the Lead Selenide (PbSe) plate detector also involves mounting a tiny chip thermistor onto the gold plated electrode of the Lead Selenide detector without coming into contact with the Lead Selenide film. The chip thermistor may be deposited onto the two gold plated electrodes which in turn are deposited with the film onto a fused quartz substrate. Such an arrangement arose from the inventor's realization that the electrode ends of the detector film are both electrically and thermally conductive. The mounting of the temperature sensor, e.g. thermistor, directly onto an electrode end places the temperature sensor at the closest position to the film on a surface that is highly thermally conductive with the film, and at the same time offering an electrical junction for sensor electrical communication. Reduced cost of circuitry and reduced space requirements are thus realized.

The above advantages over the prior art are realized in the objectives of the claimed inventions. One objective is to describe an infrared radiation detector with integrated temperature sensor comprising a substrate, on which an infrared radiation sensitive film layer is disposed, the film layer having two ends. A conductive electrode is disposed on one end of the film layer, and a conductive ground electrode is disposed on the other end of the film layer. A temperature sensor is disposed in electrical and thermal communication on the conductive ground electrode. An electrical IR detector signal lead is disposed in electrical communication with the conductive electrode and an electrical temperature signal lead disposed in electrical communication with the temperature sensor. The infrared radiation sensitive film layer preferably comprises a lead selenide (PbSe) film layer.

Standard electronics may be used as sensors and drivers such as a current source, voltage source and thermistor temperature sensor. The infrared radiation detector substrate may be quartz. The electrode and the ground electrode may be gold plated.

The temperature sensor may be a chip thermistor having a conductive pad disposed in electrical contact with the ground electrode and a second conductive pad connected to the electrical temperature signal lead, such that the chip thermistor is disposed between the ground electrode and the electrical temperature signal lead. The chip thermistor pad is connected to the electrode with a silver-filled epoxy.

The substrate may also include means for heating and cooling the substrate and film layer. The means for heating and cooling may further include a temperature control circuit having a control input from the electrical temperature signal lead.

In accordance with another object of the invention, a dual infrared radiation detector with integrated temperature sensors is described, comprising a common substrate and two infrared radiation detectors disposed adjacent to each other on the common substrate. Each radiation detector includes an infrared radiation sensitive film layer having two ends, a conductive electrode disposed on one end of the film layer, a conductive ground electrode disposed on the other end of the film layer, and a temperature sensor disposed in electrical and thermal communication on the conductive ground electrode. An electrical IR detector signal lead is disposed in electrical communication with the conductive electrode and an electrical temperature signal lead is disposed in electrical communication with the temperature sensor. Preferably, one of the infrared radiation detectors is configured to output a temperature compensated IR reference signal, and the other of the infrared radiation detectors is configured to provide a temperature compensated IR signal.

The dual infrared radiation detector with integrated temperature sensors may further comprise a heat spreader disposed in thermal contact between the common substrate and each of the radiation detectors. The dual infrared radiation detector may further comprise a circuit to receive inputs from the IR detector signal lead and the temperature signal lead of each of the two radiation detectors, and may thus provide an output of a temperature compensated carbon dioxide gas concentration as a function of the inputs. Like the single detector arrangement, the substrate may further include means for heating and cooling the substrate, which may in turn comprise a temperature control circuit having a control input from at least one of the electrical temperature signal leads and an output for controlling the temperature of the substrate.

In accordance with another aspect of the invention, a method is described for measuring a gas concentration comprising the step of providing an infrared radiation detector with integrated temperature sensor as previously described. The steps include the inputting of a constant current source to the temperature sensor via the temperature signal lead, inputting the voltage source to the film layer via the IR detector signal lead, and subsequently obtaining a temperature signal from the temperature signal lead and receiving an IR signal from the IR detector signal lead. The signals are used to compensate for a drift of the IR signal. The method outputs a measurement of a gas concentration based upon the compensating and receiving steps. The method optionally includes the amplifying of the temperature signal and the IR detector signal.

The method may further comprise the step of controlling the temperature of the substrate based upon the temperature signal from the obtaining step.

IN THE DRAWINGS

DETAILED DESCRIPTION OF THE VARIOUS EMBODIMENTS

Embodiments of the inventive apparatus described below generally includes the following main elements:

A combined function of a temperature sensor such as a chip thermistor and an IR radiation detector, such as a lead selenide plate detector, for sensing a component of a sampled gas in a temperature compensated manner;

A small size temperature sensor, such as a chip thermistor, having low thermal mass. The chip thermistor is electrically and thermally bonded to the plate detector electrode in order to closely measure the detector film temperature;

A common electrical bond between temperature sensor terminal and the IR detector terminal at a common ground; and A completed assembly with three wire bonds. One wire bond is used to output the lead selenide plate detector bias and measurement, the second wire bond to output the chip thermistor bias and measurement, and the third wire bond for the common ground for both the chip thermistor and the lead selenide detector.

In a system with two IR detectors as shown below in FIG. 2, one IR detector is arranged to sample the gas, and the other IR detector is used as a reference. Each IR detector includes its own temperature sensor. Each IR detector is also mounted onto a common (optionally) heated or cooled substrate. By this arrangement the lead selenide film temperature of each detector can be very accurately measured and tracked. This film temperature data can be used for temperature control of the common substrate by either using one detector temperature measurement or the other or an average of the two, and can be used for detector temperature compensation algorithms to maintain accuracy of the overall gas sensing, e.g. capnography, system over a wide range of ambient temperatures.

The following approach to chip thermistor/lead selenide plate detector design greatly improves the accuracy of measuring the lead selenide plate detector film temperature and improves the response time of measuring small dynamic changes in temperature between the sample and reference channel lead selenide plate detectors.

Figure 1:
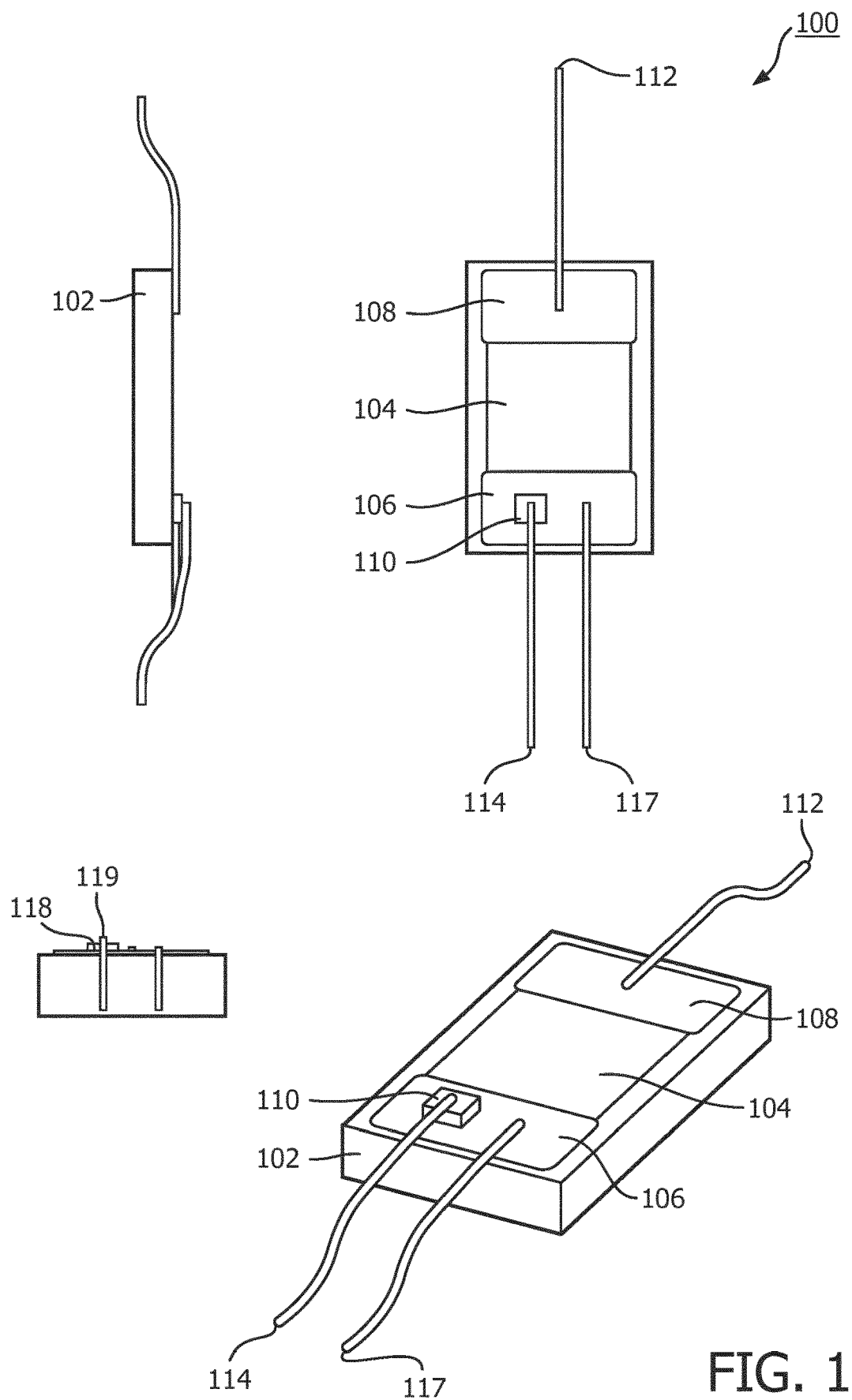
FIG. 1 illustrates one embodiment of the invention including components of a temperature sensor integrated onto an IR detector.

Now turning to the illustrations, FIG. 1 illustrates an embodiment of an infrared radiation (IR) detector with integrated temperature sensor 100. The components of detector 100 are arranged generally on a substrate 102. Substrate 102 is of a suitable substrate material for forming electrical components such as a fused quartz material. The entire detector 100 may be small in size, at 2.6×4.6 mm or smaller.

A film layer 104 comprising an infrared sensitive material may be disposed on one of the substrate surfaces by forming or adhering. A preferred IR sensitive material is lead selenide (PbSe). The lead selenide material is well known for having a resistivity that is a function of an amount of mid-range IR energy incident on the material, and thus is suitable for measuring IR radiation. The film layer 104 is shaped to have two ends, across which is placed a voltage for measuring.

Electrodes are formed by a suitable method on substrate 102, each electrode in electrical contact with one end of film layer 104. Both electrodes are conductive, one electrode designated as a conductive ground electrode 106, and the other electrode designated as a conductive electrode 108. Preferably, the electrodes are formed of a material that is highly conductive both electrically and thermally. Gold or gold-plated electrode materials are one preferable example.

FIG. 1 also illustrates an important feature of detector 100. In particular, a temperature sensor 110 is disposed directly on the surface of one of the electrodes, preferably the ground electrode 106 as shown, to be in electrical and thermal communication with the ground electrode. Such an arrangement places the temperature sensor 110 as near as possible to film layer 104 without touching the film. Because film layer 104 resistance varies with temperature in addition to IR, it is important that the temperature at the film layer is well known to a precise degree in order to compensate the IR measurement.

A preferred embodiment of the temperature sensor 110 is a thermistor. In order to keep the size small, a miniaturized chip thermistor may be used. The chip thermistor has two gold plated electrical terminals or pads. One conductive pad 118 is disposed in electrical contact with conductive ground electrode 106. Bonding between pad 118 and ground electrode 106 may be with a silver filled epoxy, which creates both an electrical and thermally conductive bond. The second conductive pad 119 on the top of the thermistor is disposed with a wire bond to a temperature signal lead 114 in order to make the electrical temperature signal connection to drive and measurement electronics. Thus, the overall arrangement is of a temperature sensor 110 sandwiched between the ground electrode 106 and the temperature signal lead 114.

Not shown in FIG. 1 but contemplated similarly to that shown in FIG. 2 and FIG. 4 below is a means for heating and cooling the substrate 102 and film layer 104. The means may comprise any of a number of heating and cooling techniques, such as electrical Ni-Chrome heating filaments disposed on the substrate and driven by an external controller, Peltier cooling/heating, passive controlled heating using a resistive heater element with an integral metal heat spreading surface (e.g. a surface mount power resistor), a heater/cooler with an intermediate metal heat spreader (e.g. a metal heat sink) to allow heat flow to/from the detector substrate, and the like. Preferably, the temperature signal is provided via the temperature signal lead to an external temperature control circuit, which in turn determines a heating or cooling input back to the substrate, at a value sufficient to maintain the desired substrate temperature. Alternatively, the temperature control circuit may reside entirely on the substrate in order to minimize assembly size.

Figure 3:
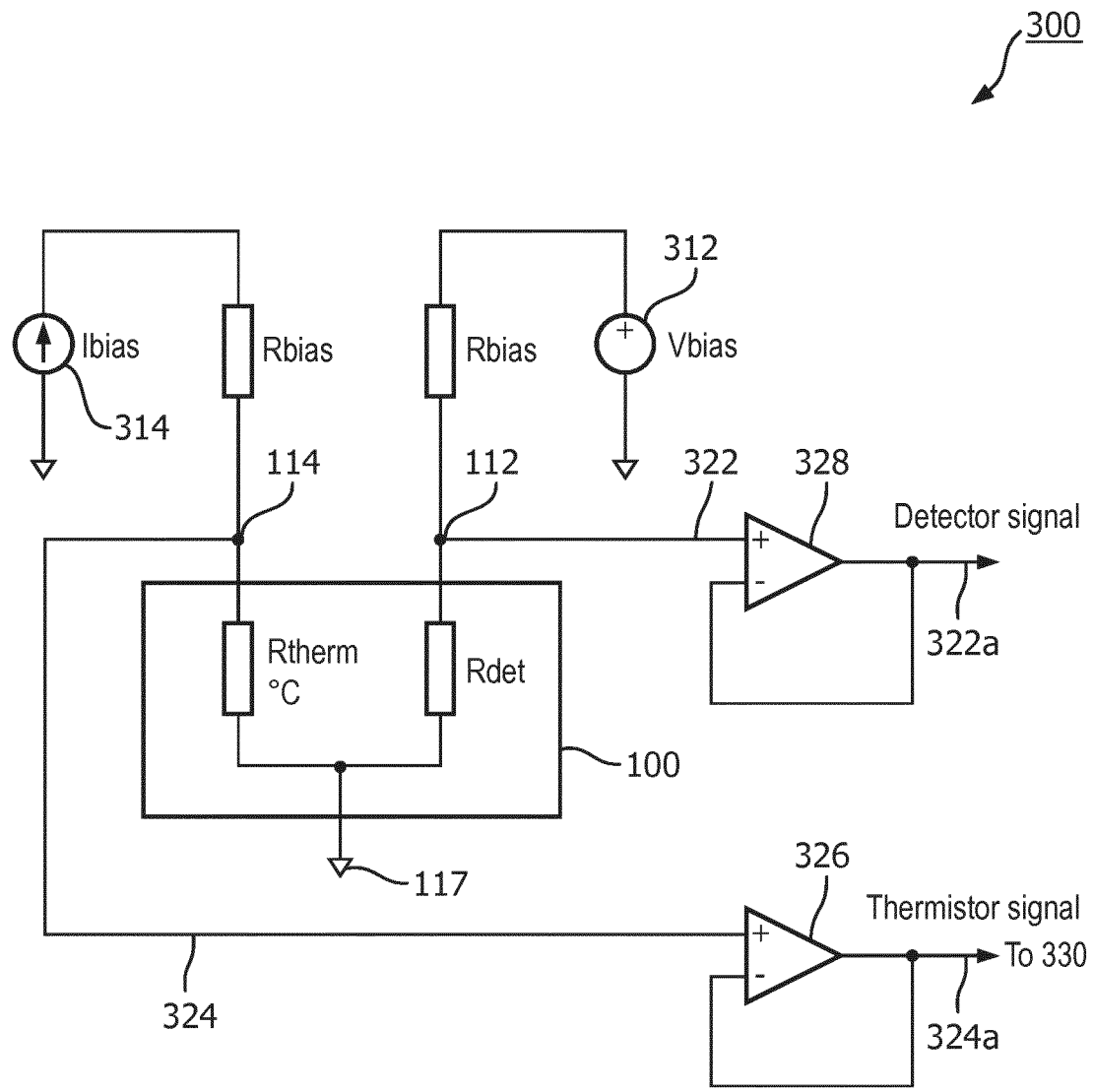
FIG. 3 illustrates an embodiment of an electrical schematic of the temperature sensor (Rtherm C) and IR detector (Rdet) assembly.

With reference to FIG. 3, the combined IR detector with integrated temperature sensor 100 (e.g. chip thermistor and lead selenide plate detector electro/thermal connection may be connected to an operating circuit 300 in the gas concentration measurement system. In particular, the circuit 300 shown there is one embodiment of a circuit for generating a temperature compensated IR signal. A noteworthy feature of circuit 300 is the common ground lead 117 shared by the temperature detector (Rtherm deg C.) and the IR detector film ground (Rdet), which is enabled by the mounting of the temperature detector conductive pad 118 directly on the ground electrode 106 on sensor 100.

One of a bias voltage or current is passed through a resistive voltage divider to energize the Lead Selenide IR detector Rdet. In the FIG. 3 embodiment the source is a voltage source 312. The resistive voltage divider is comprised of a bias resistor Rbias and IR detector resistance Rdet through to ground 117 where Rbias is selected according to the desired output range. The resulting IR signal 322 is output from the divider at the IR signal lead 112. IR signal 322 may be optionally amplified through a detector amplifier 328 or equivalent, to be further output as an amplified IR detector signal 322a. The IR detector signal may then be further used by a gas detector system, described below, to provide system control functions, to be combined with other data for further signal processing, and/or to provide output information for displays and the like.

A separate bias voltage or current is applied through another voltage divider to energize the temperature sensor chip thermistor Rtherm C. In the FIG. 3 embodiment the source is a current source 314. The circuit arrangement allows the bias current through the chip thermistor Rtherm C to be kept small, less than 50 uA. Small bias current helps to prevent self-heating of the sensor which would introduce temperature measurement errors.

The resistive voltage divider circuit for the temperature sensor 110 is comprised of another bias resistor Rbias and temperature sensor detector resistance Rtherm C through to ground 117 where this Rbias is also selected according to the desired output range. The resulting temperature signal 324 is output from the divider at the temperature signal lead 114. Temperature signal 324 may be optionally amplified through a thermistor amplifier 326 or equivalent, to be further output as an amplified temperature signal 324a. The temperature detector signal may then be further used by a gas detector system, described below, to provide system control functions, to be combined with other data for further signal processing, and/or to provide output information for displays and the like. The temperature detector signal may also be used as a substrate temperature control signal 330 in order to maintain the substrate 102 and IR detector 100 at a desired temperature.

The arrangement described above wherein the temperature sensor is directly attached to the detector electrode itself enables further reductions in measurement errors. The actual Lead Selenide IR film temperature may be is measured to better than 0.01° C. accuracy by this arrangement, allowing for improved temperature compensation algorithms to be performed in downstream capnography measurements for carbon dioxide (CO2) accuracy over a broad range of ambient temperatures that the capnography system is exposed to.

Figure 2:
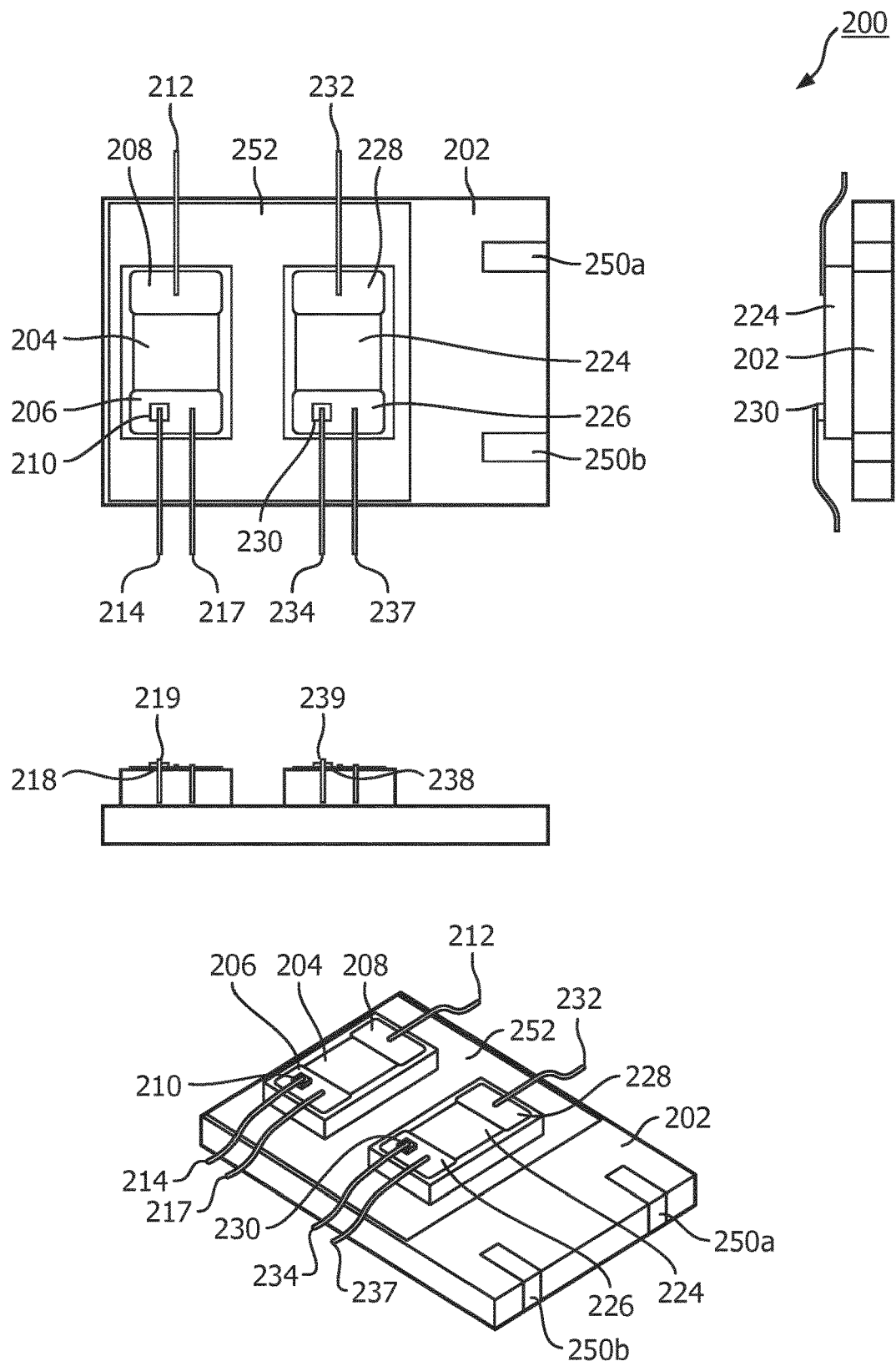
FIG. 2 illustrates one embodiment of the invention including components of a dual temperature sensor integrated onto an IR detector.

FIG. 2 illustrates one embodiment of a dual IR detector with integrated temperature sensors 200, which integrates two of the afore-described IR detectors 100 (key components of temperature sensor Chip Thermistors integrated onto IR sensitive film leads) onto a common substrate. The Dual Lead Selenide Detectors (Reference and Sample channels) thus provide parallel output signals of temperature compensated IR signals.

FIG. 2 illustrates a dual IR detector 200 with two detector assemblies fitted onto a common substrate 202. This arrangement is advantageous for gas detector assemblies which use both of a reference detector and a sample detector to simultaneously detect IR absorption characteristics of a gas stream at different frequencies. Many capnography systems use such an arrangement.

The two temperature compensated IR detector assemblies shown as arranged adjacent each other on the common substrate 202 are each constructed similarly to the previously described IR detector 100 from FIG. 1. Each assembly includes an IR radiation sensitive film layer 204, 224 which corresponds generally to IR sensitive film layer 104. Similarly, each assembly has a conductive ground electrode 206, 226, a conductive electrode 208, 228, an IR signal lead 212, 232, and a ground lead 217, 237.

Each assembly in the dual sensor 200 also includes a temperature sensor 210, 230 each sensor having a conductive pad 218, 238 and a second conductive pad 219, 239. Each of temperature sensors 210, 230 is disposed in (preferably) direct electrical and thermal contact with its respective ground electrode 206, 226 via pad 218, 238 respectively. Electrical temperature signal leads 214, 234 are disposed in electrical communication with the respective temperature sensor second conductive pad 219, 239. Embodiments of the electrodes and ground electrodes include gold plated electrodes.

An embodiment of the temperature sensors include a chip thermistor having two conductive pads, so that the chip thermistor is disposed between the respective ground electrode and the respective electrical temperature signal lead. The conductive pads 218, 238 may be connected to the respective ground electrode 206, 226 with a silver-filled epoxy.

The two detector assemblies of the dual IR detector 200 may optionally be mounted to a heat spreader 252 which is disposed on the surface of common substrate 202. The assemblies may be bonded onto the heat spreader of an actively heated or cooled substrate using a thermally conductive adhesive.

Means for heating and/or cooling the substrate 202 may be the same as used to heat or cool substrate 102 above. In one embodiment, a surface mount power resistor is adopted as the common substrate 202 (or single substrate 102) to provide only heating to some temperature above ambient. Power for heating in this embodiment is supplied via the two substrate temperature control inputs 250a, 250b from an external power supply under control of a temperature control or controller circuit 410. A control input to the control circuit 410 may be received from one or both of the electrical temperature signal leads 214, 234. An output from control circuit 410 for controlling the temperature of the substrate 202 is then used to drive the heating power input at inputs 250a, 250b. A temperature control loop results.

Either of the thermistors can be used to measure detector temperature and be used as the feedback term for the temperature control loop to maintain a constant substrate 202 temperature. Alternatively, the average temperature from both chip thermistors could be used for the feedback temperature value in the temperature control loop.

Even with both temperature compensated IR detectors 204/210, 224/230 (e.g. Chip Thermistor Lead Selenide Detectors) mounted to a common substrate 202, the substrate will experience some degree of differential temperature gradients across the mounting substrate heater or cooler. These temperature gradients may be accounted for and can be algorithmically compensated for in real-time in the measurement and control system to maintain overall capnometer system accuracy over a wide ambient operating range. The mounting of the chip thermistor as close as possible to the detector film deposition layer enables the film temperature to be measured to better than $0.01°$ C. accuracy for each of the two detectors. Any mismatch or drift in temperature between the two detectors is accurately measured by this arrangement, enabling the downstream processing and control circuits to apply very accurate temperature corrections to the IR signal.

An electrical control circuit of FIG. 3 for generating temperature compensated IR signals 300 was previously described. Such a circuit may be easily adopted for each of the IR detector assemblies in the dual IR detector 200.

Figure 4:
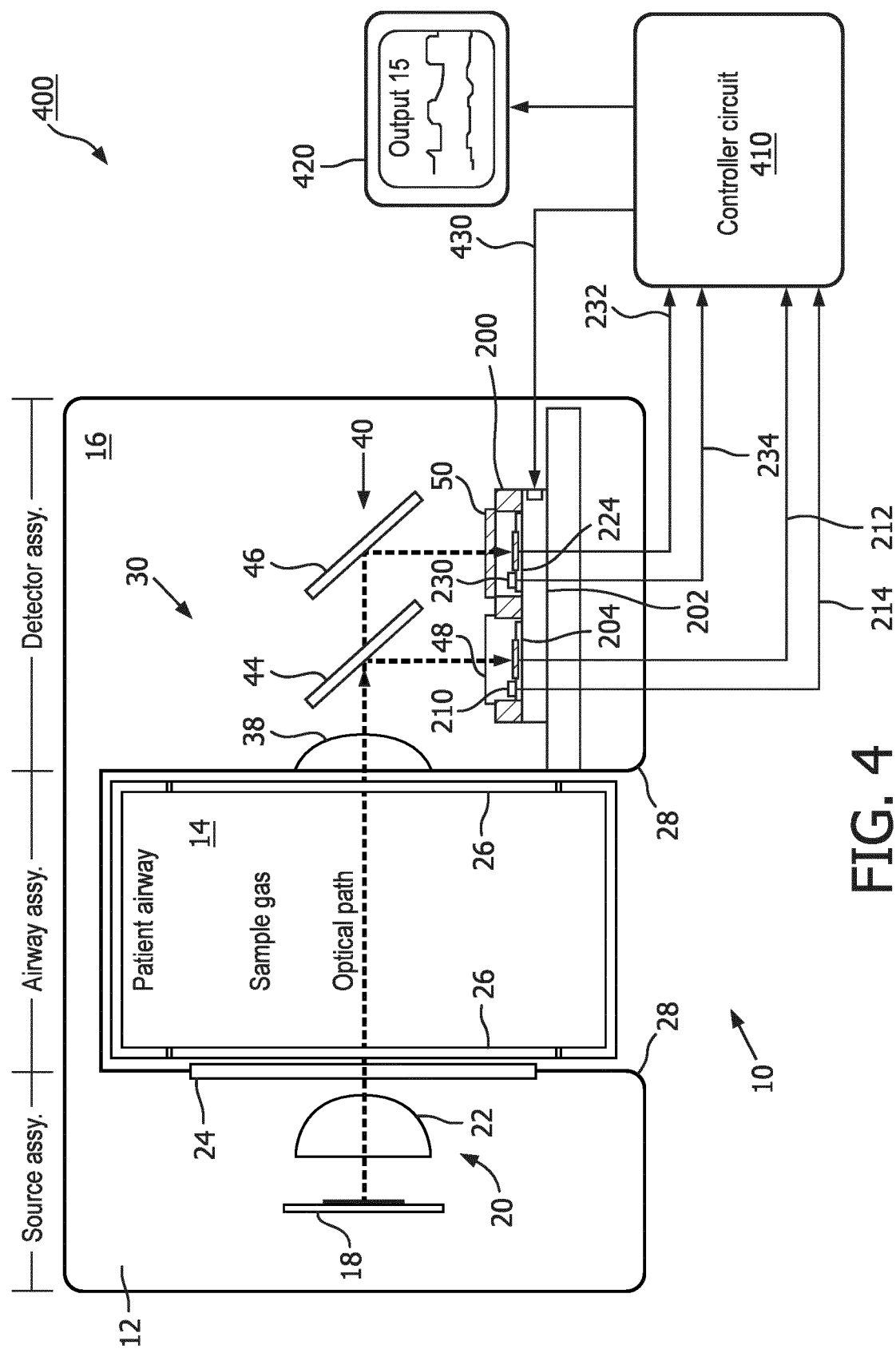
FIG. 4 illustrates an embodiment of an improved capnography system which includes dual IR detector with an integrated temperature sensor.

FIG. 4 illustrates a carbon dioxide gas detector system 400 which integrates the improved IR detector 200 in its assembly. The overall system, excluding improved detector 200, is somewhat similar to the assembly described in co-assigned U.S. Patent Publication No. 2013/0292570 entitled "System and method for performing heater-less lead selenide-based capnometry and/or capnography", which is herein incorporated by reference. A sensor assembly 10 is configured to detect a level of carbon dioxide in a body of gas. The sensor assembly 10 employs the afore-described dual IR detector with integrated temperature sensors 200. In this embodiment, infrared radiation detector 204 is arranged to capture an IR signal, and infrared radiation detector 224 is arranged to capture an IR reference signal. The detectors 204/224 may be lead selenide detectors. Measurements of sensor device 10 are compensated for variations in temperature at detector 200 via one or both of temperature sensors 210 or 230 as previously described. This may reduce the cost, enhance stability, enhance ruggedness, enhance manufacture and/or provide other advantages over prior sensor devices.

In one embodiment, sensor device 10 includes a "U" shaped housing 28 enclosing a source assembly 12, a hollow airway assembly 14, a detector assembly 16, and/or other components. Two opposing legs of the "U" shaped housing 28 define opposite sides of a gap there-between, with the source assembly 12 disposed in one leg on one side of the gap (source side) and the detector assembly 16 disposed in the opposing leg on the opposite side of the gap (detector side). The sensor device 10 may include self-contained electronics (not shown in FIG. 4) disposed within the housing 28.

The airway assembly 14 has windows 26 disposed on opposite sides such that infrared radiation entering the airway via the window 26 on one side of the airway 14 passes through a sample gas (patient respiration) in the airway 14 and exits via the window 26 on the opposite side. The airway assembly 14 may be either a disposable unit or a reusable unit that removably clips into the gap in the "U" shaped housing, with the source assembly 12 and detector assembly 16 being generally arranged such that infrared radiation emanating from the source assembly is directed across the gap through the gas sample in the airway assembly 14 to impinge upon the detector assembly 16. The airway windows 26 may be formed of plastic film (disposable version), sapphire (reusable version) and/or other materials.

The source assembly 12 includes a radiation source 18, optics 20, and/or other components. The emitter 18 may be driven by a pulsed source of energy to produce pulsed infrared radiation. The optics 20 may include a sapphire half-ball lens 22, a sapphire window 24, and/or other optical components. The radiation source 18 produces broadband radiation including an "MWIR" (Mid-Wavelength Infra-Red) band. Infrared radiation generally refers to radiation occupying a band of wavelengths in the optical spectrum between 0.7 µm and 300 µm. "MWIR" generally refers to a mid-wavelength subset of the infrared radiation band between 3 µm and 8 µm. MWIR radiation emitted by the radiation source 18 includes a reference wavelength and a carbon dioxide wavelength ($\lambda$REF and $\lambda$CO2, respectively). The radiation source 18 may be pulsed at about 100 Hz to produce a periodically varying MWIR signal with a period of about 10 milliseconds. The sapphire half-ball lens 22 gathers and collimates the emitted radiation, directing it across the gap and through the airway assembly 14 towards the detector assembly 16 via the sapphire window 24.

The detector assembly 16 includes optics 30, dual IR detector with integrated temperature sensors 200, and/or other components. Optics 30 comprise a lens assembly 38, a beam splitter assembly 40, and/or other optical components. The lens assembly 38, which in one embodiment includes an AR-coated (Anti-Reflective coated) silicon plano-convex lens, focuses the MWIR radiation reaching it from the source assembly 12, and directs the electromagnetic radiation toward first IR radiation detector 204 and second IR radiation detector 224 via beam splitter assembly 40. In beam splitter assembly 40, a dichroic beam-splitter 44 is positioned to reflect IR radiation containing the carbon dioxide wavelength $\lambda$CO2 towards first IR detector 204, and to pass IR radiation containing the reference wavelength $\lambda$REF towards second IR detector 224 via a turning mirror 46. A narrow-band first optical filter 48 that passes $\lambda$CO2 is positioned in front of first IR detector 204. A narrow-band second optical filter 50 that passes $\lambda$REF is positioned in front of second IR detector 224.

As previously described, first and second IR detectors 204, 224 are mounted to common substrate 202, which may further have a common heat spreader 252 (shown in FIG. 2).

IR signal outputs from IR signal leads 212, 232 provide IR signal and IR reference signals respectively to a gas detector controller circuit 410. Temperature signal outputs from temperature signal leads 214, 234 provide temperature signals from each of the IR detectors to controller 410 as well. Controller 410 processes signals 212, 232, 214, and 234 to obtain a temperature-compensated IR signal and a corresponding temperature-compensated carbon dioxide gas concentration value from the sample gas crossed by the optical path. Controller 410 further outputs the carbon dioxide value to an output 420, which may be a visual display.

Controller 410 may optionally provide a temperature control output that is a function of signals 214 and 234 in order to maintain the temperature of detector 200 at a desired value. The temperature control output is experienced by detector 200 as input 430 to temperature control inputs 250a, 250b (FIG. 2). The temperature control algorithm may be any of that described herein, equivalents, or as known in the art.

Also in accordance with the principles of the present invention, a method is described which incorporates the above summarized apparatus to measure a lead selenide plate detector temperature, and which results in an improved and quicker temperature measurement.

Figure 5:
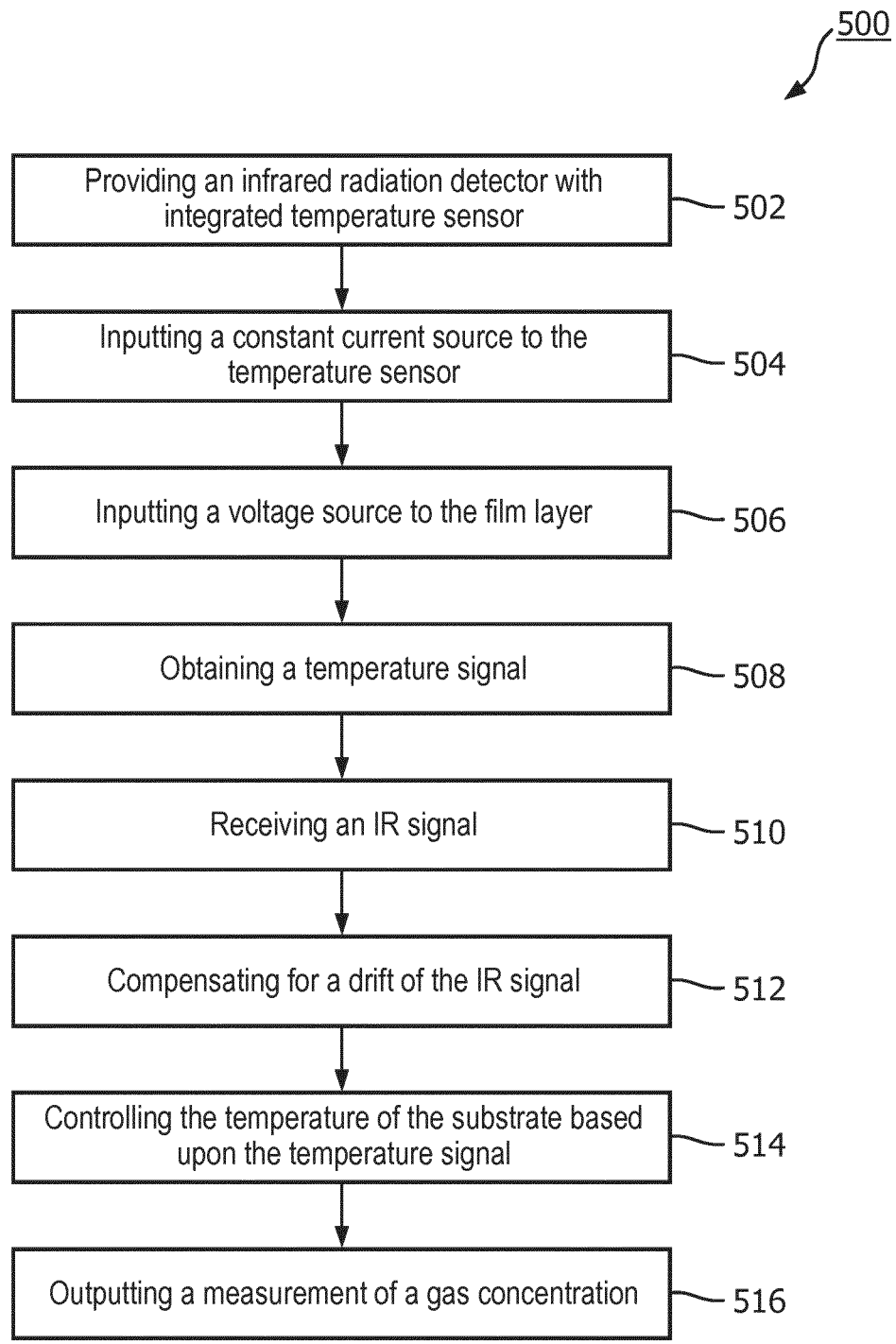
FIG. 5 is a flow chart illustrating a method of the present invention.

Controller 410 preferably includes the circuitry as shown in FIG. 3 to provide the functions and steps involved in a method 500, shown in FIG. 5, for measuring a gas concentration. The method begins with a first step of providing 502 an infrared radiation detector with integrated temperature sensor as described previously and in relation to FIG. 1 and/or FIG. 2. Controller 410 then provides a step of inputting a constant current source 504 to one or more of the temperature sensors via the temperature signal lead(s), and a step of inputting a voltage source 506 to one or more of the film layers via the IR detector signal lead(s). detector 100 or dual detector 200 responsively provide outputs of temperature and IR signals from leads 114, 204, 234 and 112, 212, 232 respectively. Controller 410 receives the outputs in the obtaining step of obtaining a temperature signal 508 from the temperature signal lead and the receiving step of receiving an IR signal 510 from the IR detector signal lead. The obtaining step may further include amplifying the temperature signal, and the receiving step may further include amplifying the IR detector signal, both amplifying by means of amplifying circuits 326, 328 (FIG. 3).

Controller 410 further executes a step of compensating for a drift of the IR signal 512 from the receiving step based on the obtaining step. Controller 410 then provides the step of outputting a measurement of a gas concentration 516, preferably to output 420, based upon the compensating and receiving steps.

Controller 410 optionally executes a step of controlling the temperature of the substrate 514 based upon the temperature signal from the obtaining step. As previously described, controller 410 may use one or more temperature inputs 114, 214, 234 to provide a control input 430 to the substrate, wherein input 430 provides heating or cooling energy to maintain the substrate at a controlled and desired temperature.

Modifications to the device, method, and displays as described above are encompassed within the scope of the invention. For example, various configurations of the temperature detector which fulfill the objectives of the described invention fall within the scope of the claims. Also, the particular appearance and arrangement of the apparatus may differ, as well as the location and disposition of various circuit elements and sensors.

Table of Elements

| Number | Name |
|---|---|
| 100 | IR detector with integrated temperature sensor |
| 102 | substrate |
| 104 | IR sensitive film layer |
| 106 | conductive ground electrode |
| 108 | conductive electrode |
| 110 | temperature sensor |
| 112 | IR signal lead |
| 114 | temperature signal lead |
| 117 | ground lead |
| 118 | conductive pad |
| 119 | second conductive pad |
| 200 | dual IR detector with integrated temperature sensors |
| 202 | common substrate |
| 204 | infrared radiation detector |
| 206 | conductive ground electrode |
| 208 | conductive electrode |
| 210 | temperature sensor |
| 212 | IR signal lead |
| 214 | temperature signal lead |
| 217 | ground lead |
| 218 | conductive pad |
| 219 | second conductive pad |
| 224 | infrared radiation detector |
| 226 | conductive ground electrode |
| 228 | conductive electrode |
| 230 | temperature sensor |
| 232 | IR signal lead |
| 234 | temperature signal lead |
| 237 | ground lead |
| 238 | conductive pad |
| 239 | second conductive pad |
| 250a | substrate temperature control input |
| 250b | substrate second temperature control input |
| 252 | heat spreader |
| 300 | circuit for generating temperature compensated IR signal |
| 312 | voltage source |
| 314 | current source |
| 322 | IR signal |
| 322a | amplified IR signal |
| 324 | temperature signal |
| 324a | amplified temperature signal |
| 326 | thermistor amplifier |
| 328 | detector amplifier |
| 330 | substrate temperature control signal |
| 400 | gas detector |
| 410 | gas detector controller circuit |
| 420 | gas detector output |
| 430 | gas detector temperature control input |
| 500 | method for measuring a gas concentration |
| 502 | providing an IR radiation detector with integrated temperature sensor step |
| 504 | inputting a constant current source to the temperature sensor step |
| 506 | inputting a voltage source to the film layer step |
| 508 | obtaining a temperature signal step |
| 510 | receiving an IR signal step |
| 512 | compensating for a drift of the IR signal step |
| 514 | controlling the temperature of the substrate based upon the temperature signal step |
| 516 | outputting a measurement of a gas concentration step |

What is claimed is:

1. An infrared radiation detector with integrated temperature sensor comprising:
    a substrate;
    an infrared radiation sensitive film layer disposed on the substrate, the film layer having two ends;
    a conductive electrode disposed on one end of the film layer;
    a conductive ground electrode disposed on the other end of the film layer;
    a temperature sensor disposed in electrical and thermal communication with the conductive ground electrode;
    an electrical IR detector signal lead disposed in electrical communication with the conductive electrode and an electrical temperature signal lead disposed in electrical communication with the temperature sensor.

2. The infrared radiation detector of claim 1, wherein the infrared radiation sensitive film layer comprises a lead selenide (PbSe) film layer.

3. The infrared radiation detector of claim 1, further comprising:
a current source disposed in electrical communication with the temperature sensor, wherein the temperature sensor is a thermistor.

4. The infrared radiation detector of claim 1, wherein the substrate is quartz.

5. The infrared radiation detector of claim 1, wherein the electrode and the ground electrode are gold plated, and further wherein the temperature sensor is a chip thermistor having a conductive pad disposed in electrical contact with the ground electrode and a second conductive pad connected to the electrical temperature signal lead, such that the chip thermistor is disposed between the ground electrode and the electrical temperature signal lead.

6. The infrared radiation detector of claim 5, wherein the chip thermistor pad is connected to the ground electrode with a silver-filled epoxy.

7. The infrared radiation detector of claim 1, wherein the substrate includes means for heating and cooling the substrate and film layer.

8. The infrared radiation detector of claim 7, wherein the means for heating and cooling further comprise a temperature control circuit having a control input from the electrical temperature signal lead.

9. A dual infrared radiation detector with integrated temperature sensors, comprising:
a common substrate;
two infrared radiation detectors disposed adjacent to each other on the common substrate, each radiation detector including
an infrared radiation sensitive film layer having two ends, a conductive electrode disposed on one end of the film layer, a conductive ground electrode disposed on the other end of the film layer, a temperature sensor disposed in electrical and thermal communication with the conductive ground electrode, an electrical IR detector signal lead disposed in electrical communication with the conductive electrode and an electrical temperature signal lead disposed in electrical communication with the temperature sensor,
wherein one of the infrared radiation detectors is configured to output a temperature compensated IR reference signal, and the other of the infrared radiation detectors is configured to provide a temperature compensated IR signal.

10. The dual infrared radiation detector with integrated temperature sensors of claim 9, further comprising a heat spreader disposed in thermal contact between the common substrate and each of the radiation detectors.

11. The dual infrared radiation detector of claim 9, further comprising a circuit to receive inputs from the IR detector signal lead and the temperature signal lead of each of the two radiation detectors and to provide an output of a temperature compensated carbon dioxide gas concentration as a function of the inputs.

12. The dual infrared radiation detector of claim 9, wherein the substrate further includes means for heating and cooling the substrate.

13. The dual infrared radiation detector of claim 12, wherein the means for heating and cooling further comprise a temperature control circuit having a control input from at least one of the electrical temperature signal leads and an output for controlling the temperature of the substrate.

14. The dual infrared radiation detector of claim 9, wherein each of the electrode and the ground electrode are gold plated, and further wherein each of the temperature sensors is a chip thermistor having a conductive pad disposed in electrical contact with the respective ground electrode and a second conductive pad connected to the respective electrical temperature signal lead, such that each chip thermistor is disposed between the respective ground electrode and the respective electrical temperature signal lead.

15. The dual infrared radiation detector of claim 14, wherein each of the chip thermistor pads is connected to the respective ground electrode with a silver-filled epoxy.

16. A method for measuring a gas concentration, comprising the steps of:
providing an infrared radiation detector with integrated temperature sensor as described in claim 1;
inputting a constant current source to the temperature sensor via the temperature signal lead;
inputting a voltage source to the film layer via the IR detector signal lead;
obtaining a temperature signal from the temperature signal lead;
receiving an IR signal from the IR detector signal lead;
compensating for a drift of the IR signal from the receiving step based on the obtaining step; and
outputting a measurement of a gas concentration based upon the compensating and receiving steps.

17. The method of claim 16, wherein the obtaining step further includes amplifying the temperature signal, and wherein the receiving step further includes amplifying the IR detector signal.

18. The method of claim 16, further comprising the step of controlling the temperature of the substrate based upon the temperature signal from the obtaining step.

* * * * *